US012740930B2

(12) United States Patent
Kim et al.

(10) Patent No.: US 12,740,930 B2
(45) Date of Patent: Sep. 22, 2026

(54) COMPOSITION FOR TREATING HAIR OR FIBERS, COMPRISING ALKYL KETENE COMPOUND

(71) Applicant: LG HOUSEHOLD & HEALTH CARE LTD., Seoul (KR)

(72) Inventors: Dae Hyun Kim, Seoul (KR); Seong Kil Son, Seoul (KR); Nae Gyu Kang, Seoul (KR); In-Ho Lee, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 703 days.

(21) Appl. No.: 18/012,702

(22) PCT Filed: Apr. 14, 2021

(86) PCT No.: PCT/KR2021/004711
§ 371 (c)(1),
(2) Date: Apr. 28, 2023

(87) PCT Pub. No.: WO2021/261726
PCT Pub. Date: Dec. 30, 2021

(65) Prior Publication Data

US 2023/0263718 A1 Aug. 24, 2023

(30) Foreign Application Priority Data

Jun. 25, 2020 (KR) ........................ 10-2020-0077851

(51) Int. Cl.
*A61K 8/49* (2006.01)
*A61Q 5/12* (2006.01)

(52) U.S. Cl.
CPC .............. *A61K 8/4973* (2013.01); *A61Q 5/12* (2013.01); *A61K 2800/596* (2013.01)

(58) Field of Classification Search
None
See application file for complete search history.

(56) References Cited

U.S. PATENT DOCUMENTS

| | | | | |
|---|---|---|---|---|
| 2,791,484 | A | 5/1957 | Cafasso | |
| 5,132,028 | A | 7/1992 | Nagase et al. | |
| 5,275,625 | A | 1/1994 | Rebouillat | |
| 2001/0053377 | A1* | 12/2001 | Mondet .................. | A61K 8/893 424/401 |
| 2014/0315461 | A1 | 10/2014 | Schachtner et al. | |

FOREIGN PATENT DOCUMENTS

| | | | |
|---|---|---|---|
| CN | 105062107 | A | 11/2015 |
| JP | 60-115508 | A | 6/1985 |
| JP | 2796385 | B2 | 9/1998 |
| JP | 2013-514265 | A | 4/2013 |
| JP | 2015-502460 | A | 1/2015 |
| KR | 10-2009-0090138 | A | 8/2009 |
| WO | WO 98/40046 | A2 | 9/1998 |
| WO | WO 2008/156327 | A2 | 12/2008 |

OTHER PUBLICATIONS

Machine Translation of JPS60115508A (Year: 1985).*
International Search Report (PCT/ISA/210), issued in PCT/KR2021/004711, mailed Jul. 16, 2021.

* cited by examiner

*Primary Examiner* — Jennifer A Berrios
(74) *Attorney, Agent, or Firm* — Birch, Stewart, Kolasch & Birch, LLP

(57) ABSTRACT

The present invention relates to composition for hair or fiber comprising an alkyl ketene compound.

The composition according to the present invention includes an alkyl ketene compound capable of covalently bonding with a protein residue on a surface of hair or fibers, and the alkyl ketene compound can form a covalent bond with the hair or fiber to provide beneficial effects, such as long-lasting conditioning.

9 Claims, No Drawings

COMPOSITION FOR TREATING HAIR OR FIBERS, COMPRISING ALKYL KETENE COMPOUND

TECHNICAL FIELD

The present invention relates to composition for hair or fiber comprising an alkyl ketene compound.

BACKGROUND ART

In general, hair cosmetics impart beneficial properties, such as smoothness, softness, ease of combing, volume, relaxation, and styling to hair to beautify hair, increase attractiveness, change appearance, and are intended to be applied, spread, and used in similar ways on hair to keep hair healthy.

Hair conditioning should be a continuous process. Hair is basically a dead cell derived from a small number of living cells deep in the skin surface. Therefore, hair conditioning components have no substantial effect on cell growth and cannot affect underlying cell repair. Thus, since hair conditioning temporarily improves the properties of damaged hair, a hair conditioner needs to be reapplied again and again.

Damage to hair by physical and chemical treatment causes changes in the physical structure of hair. Conditioning components cannot fundamentally heal hair, but they can temporarily increase the cosmetic value and function of hair until the conditioner is removed by cleansing with a detergent. Therefore, it is a very important characteristic that the conditioning components remain on the hair for a long time without being removed even when a detergent is used, and that the effect is maintained.

Most hair damage is caused by hair care habits, such as shampooing, drying, combing, styling, conditioning, and perming for cosmetic purposes, exposure to chemicals and environmental factors, such as sunlight, air pollution, wind, seawater and chlorinated swimming pools. Conditioners can enhance the cosmetic value of weathered hair through several types of mechanisms, including reducing static electricity, enhancing hair strength, protecting against UV radiation, and increasing gloss.

In the present invention, hair treatment includes reducing the breakage and porosity of hair and increasing strength and gloss to alleviate, prevent, or recover from hair damage from various damage factors, such as heat, dyeing, perming, washing, and ultraviolet rays. Conditioners using cationic surfactants or cationic polymer components are very efficient conditioning components because of the affinity directly involved in electrical interaction between the surfactant or polymer and the opposite charge on the surface of the hair. Conditioners generally remain on the surface of the hair strands to reduce friction and flyaways when combing and to make the hair feel soft and supple. In some other systems, the conditioner imparts volume enhancement, curl retention, hair volume, ease of grooming, and the like, and these properties are also included in the hair treatment of the present invention.

In addition, recent conditioners are designed to provide ease of combing wet and dry hair, provide softness by filling and rearranging damaged hair, minimize porosity, give hair a silky feel by giving luster, and provide one or more of the following functions: protection against heat and mechanical damage, moisturizing, imparting volume and thickening, dissipating static electricity, and these properties are also included in the hair treatment of the present invention.

In general, the human hair cuticle consists of flat, overlapping cells (scales). Cuticle cells are attached like roof tiles from the root to the tip of the hair fiber. Each cuticle layer has a thickness of about 0.3 to 0.5 μm, and a part of the cuticle that is visible among them is about 5 to 10 μm. The cuticle of human hair is generally made up of 5 to 10 layers. Each cuticle cell of the hair is composed of various sublamellar layers, such as the epicuticle, A-layer, exocuticle, endocuticle, inner layer, and a cell membrane complex. The outermost epicuticular layer is covered with covalently bound lipids (fatty acids), and the most abundant lipid component is 18-methyl eicosanoic acid (18-MEA). This layer constitutes the outer (3-layer of the cuticle cell membrane complex and has functions, such as lubrication, friction reduction, and formation of a hydrophobic surface.

The part of the hair that protrudes outside the scalp is called the hair shaft, and this part changes according to the lifetime and length of the hair. In addition, it is changed by hair cutting, shampooing, drying, combing, perming, hair coloring, and the like, or environmental stress such as dryness, ultraviolet rays, seawater, and lime in the pool. In particular, even when it is not directly affected by the above types of stress, the hair cuticle surrounding the outside of the hair shaft is damaged when they accumulate in a complex manner. In damaged hair, a tip of the hair cuticle protrudes or is partially peeled off, so fallout is further progressed. Such hair loses luster and becomes unsmooth because light is diffusely reflected. When the damage to hair progresses further, the hair cuticle layer completely separates, exposing the inner cortex, and eventually the hair becomes easily split or broken.

In this way, various treatments have been attempted to improve the surface of damaged hair due to loss of 18-MEA. In particular, products that provide a conditioning effect to hair, such as hair manicure or hair essence that coats the surface of hair using silicone, are sold or treated through beauty salons. However, when these conditioning components are used for hair, it only provides a temporary and short-term effect until the next washing after treatment, but there is always the hassle of re-treatment after washing.

Patent Document 1 relates to a non-aqueous personal care product for skin or hair, and discloses conditioning components having one or more selected from the group consisting of carbonate, aldehyde, propionaldehyde, butylaldehyde, nitrophenyl carbonate, aziridine, isocyanate, thiocyanate, epoxide, tresylate, succinimide, hydroxysuccinimidyl ester, imidazole, oxycarbonylamidazole, imine, thiol, maleimide, vinylsulfone, ethyleneimine, thioether, acrylonitrile, acrylic acid, methacrylic ester, disulfide, ketone, and a functional group represented by Rx (RR is any one selected from the group consisting of an alkyl, an aralkyl, a ring, and an unsaturated ring, and x is I, Br, or CO, which is a functional group capable of covalently bonding with a protein residue on the surface of the hair or skin. In addition, personal care products for hair or skin include the conditioning components, are separated into a non-aqueous part and an aqueous part, and are characterized in that they are mixed and used immediately before use. In the case of the various functional groups, since the functional group reacts by targeting a small amount of lysine (1.9-3.1% in hair, 3.1-6.9% in skin keratin) or cysteine (16.6-18% in hair, 2.3-3.8% in skin keratin) among amino acids of proteins that are harmful to the human body or constitute hair or skin, there is a problem that reaction efficiency is lowered and each material needs to be synthesized separately.

In the present invention, functions of the fiber treatment agent refer to the following functions: imparting a softening effect to fibers, preventing light damage, inhibiting formation of wrinkles in fibers, removing formed wrinkles easily, changing the original color of fibers, maintaining the original color for a long time, enabling easy removal of surface contamination, giving a fragrance, removing an odor, providing antibacterial or pest-repellent properties, preventing damage caused by washing, or preventing the penetration of rainwater.

In the present invention, the fiber treatment composition generally includes a composition for cleaning, tidying, pointing, and the like for fiber care, and a composition for providing beneficial functions to the fiber, such as dyeing, bleaching, softening, sterilization, UV protection, and fragrance.

Products formulated with such compositions include detergents, softeners, fiber rinses, treatment or partial treatment agents, and the like.

Common raw materials used to form such a fiber care composition include oil-based raw materials, such as fats and oils, waxes, hydrocarbons, higher fatty acids, higher alcohols, ester oils and silicone oils, anionic, cationic, amphoteric, nonionic surfactants, polymer compounds used as moisturizers, thickeners and film formers, UV absorbers and blockers, antioxidants, sequestering agents, ion exchangers, builders, bleaches, enzymes, foam control agents, fluorescent whitening agents, anti-migration agents, coloring materials, such as dyes and pigments, fragrances and preservatives.

In addition, fiber care components for providing special performance may include components having the following functions: imparting a softening effect to fibers, preventing light damage, inhibiting formation of wrinkles in fibers, removing formed wrinkles easily, changing the original color of fibers, maintaining the original color for a long time, enabling easy removal of surface contamination, giving a fragrance, removing an odor, providing antibacterial or pest-repellent properties, preventing damage caused by washing, or preventing the penetration of rainwater, and the components may specifically include soap, alkylbenzene sulfonate, alkane sulfonate, alpha olefin sulfonate, alpha sulfo fatty acid ester, alkyl sulfate, alkylether sulfate, alcohol toxylate, alkylphenol ethoxylate, fatty acid alkanolamide, alkylamine oxide, methyl glucamide, alkyl polyglucoside, distearyldimethylammonium chloride, imidazolinium derivative, alkyldimethylbenzene ammonium chloride, esterquats, aminoester salt, alkylbetaine, alkylsulfobetaine, sodium carbonate, calcium carbonate, sodium silicate, sodium triphosphate, nitrotriacetic acid, polycarboxylate, zeolite, sodium polycarboxylate, sodium polyacrylate, sodium hyrdroxyethane diphosphate, sodium perborate, sodium percarbonate, peroxide, hypochlorite, tetraacetylethylenediamine, sodium para-nonanoyloxybenzenesulfonate, sodium percarbonate, sodium perborate, proteolytic enzymes, lipolytic enzymes, starch degrading enzymes, pectin degrading enzymes, cellulolytic enzymes, carboxymethyl cellulose, carboxymethyl starch, cellulose ether, polyethylene terephthalic acid/polyoxyethylene terephthalic acid copolymers, fatty acid amide, fatty acid alkanolamide, amine oxide, stilbene, coumarin, bisbenzazole, distyrylbiphenyl, polyvinylpyrrolidone, polyvinylpyridine oxide, a fragrance, cyclodextrin, sodium sulfate, silicone and derivatives, alkylamines, fatty alcohols, fatty acids, polyethylene, magnesium chloride, calcium chloride, sodium chloride and sodium acetate, and the like.

However, when such fiber care components are used for fibers, only a temporary effect is provided until the next cleaning after treatment, and there is always the hassle of re-treatment after cleaning.

Patent Document 2 discloses a makeup treatment method that maintains makeup properties for a long time on hair having similar components to wool fiber. In the above technology, it is necessary to perform a process of first activating the hair through physical methods, such as heat, electromagnetic waves, electric fields, sound waves, and plasma, or chemical methods other than reduction methods to change the surface of the hair before hair makeup treatment. However, this hair activation process requires high energy, such as heat, electromagnetic waves, electric fields, sound waves and plasma to be applied to the hair, and oxidizing agents, such as hydrogen peroxide and bromate, which are used as chemical inactivation substances other than reducing agents, cause severe damage to the hair. In the case of other polyamines or polysaccharide polymers, activation is possible, but these polymers are not activated in the form of a covalent bond to hair, so there is a problem that they are easily removed by washing.

In addition, Patent Document 3 considered a method of microencapsulating and adding a fragrance while using chitosan, which is an antibacterial component, in order to provide excellent durability of a fragrance and antibacterial properties to fibers in addition to a softening effect on fibers. In this way, when the fragrance is treated using microcapsules, the capsule protects the fragrance, which is a core material, from an external environment to improve storage stability, so there is an advantage in that durability of the fragrance in the fiber is excellent. On the other hand, since this fragrance capsule also does not remain on the surface of the fiber during a washing process and is mostly washed away, there is a limit to providing an effect only with a capsule component remaining on some fibers, and even economically, most of the used capsules do not function properly and have a problem of being rinsed out with rinse water.

RELATED ART DOCUMENT

Patent Document

1. Patent Document 1: Korean Patent Publication No. 2008-0064467
2. Patent Document 2: Japanese Laid-open Patent No. 2004-182731
3. Patent Document 3: Korean Patent Publication No. 2002-0068427

DISCLOSURE

Technical Problem

The present invention is directed to providing a hair or fiber treatment composition capable of sustaining beneficial effects, such as conditioning for a long time without damaging hair or fibers.

The present invention is also directed to providing a hair or fiber treatment composition capable of maintaining a residual fragrance in the hair or fibers and enhancing flexibility, softness, hydrophobicity and/or an anti-shrinkage property.

Technical Solution

As a means for solving the above problems, the present invention provides a hair or fiber treatment composition including an alkyl ketene compound represented by Chemical Formula 1 below.

[Chemical Formula 1]

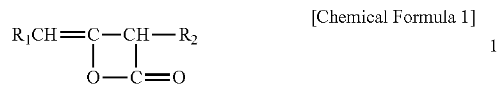

in Chemical Formula 1, $R_1$ and $R_2$ are each independently a saturated or unsaturated alkyl having 1 to 40 carbon atoms or a saturated or unsaturated fatty acid having 1 to 40 carbon atoms.

In addition, the present invention provide a method of conditioning hair or fibers, including treating hair or fibers with the hair or fiber treatment composition. The method may further include a heat treatment step.

In addition, the present invention provides a hair or fiber treatment product for preventing or improving thermal damage, including the hair or fiber treatment composition.

In addition, the present invention provides the use of a composition including an alkyl ketene compound represented by the above-described Chemical Formula 1 for preparing a hair or fiber treatment product.

Advantageous Effects

Since a hair or fiber treatment composition according to the present invention contains an alkyl ketene compound capable of covalently bonding with protein residues of hair or fibers, the alkyl ketene compound forms a covalent bond with the protein residues without damaging hair or fibers, and beneficial effects, such as long-lasting conditioning can be provided by imparting permanent hydrophobicity.

In addition, the hair or fiber treatment composition according to the present invention can prevent and/or improve damage to hair or fibers caused by heat.

In addition, the hair or fiber treatment composition according to the present invention can maintain a residual fragrance in hair or fibers, and can enhance flexibility, softness, hydrophobicity or an anti-shrinkage property.

MODES OF THE INVENTION

The present invention relates to a hair or fiber treatment composition including an alkyl ketene compound represented by Chemical Formula 1 below.

In addition, the present invention relates to use of a composition including an alkyl ketene compound represented by the following Chemical Formula 1 for preparing a hair or fiber treatment product.

[Chemical Formula 1]

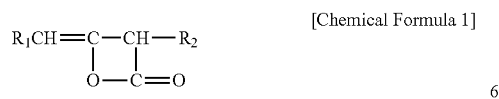

Hereinafter, the configuration of the present invention will be described in detail.

The hair or fiber treatment composition according to the present invention contains an alkyl ketene compound, and the alkyl ketene compound forms a covalent bond with hair or fibers, thereby maximizing a conditioning effect and maintaining the effect for a long time. In addition, it is possible to prevent damage to hair or fibers caused by heat. That is, the hair or fiber treatment composition according to the present invention can be used as a conditioning composition for hair or fibers.

In the present invention, the "conditioning" effect is to beautify hair or fibers by imparting beneficial properties, such as ease of combing, smoothness, softness, relaxation, gloss and volume, increase attractiveness, change the appearance of hair or fibers, and in order to keep the hair or fibers healthy, it is applied to the body (hair) or fiber by application, spreading, and other methods similar thereto, and a conditioning effect may include, for example, imparting gloss and luster, reducing static electricity, and the like. In addition, by making the surface of the hair or fiber hydrophobic, it prevents the penetration of moisture from an external environment into the hair, and also prevents the moisture inside the hair or fiber from escaping to the outside to help maintain moisture in the hair or fiber. In addition, it is possible to prevent the elution of protein components inside the hair or fiber by washing due to damage to the hair and protein-based fibers (wool, silk, and the like). Therefore, effects of not only relieving or recovering from symptoms of damaged hair or damaged fibers, but also ultimately preventing damage to the hair or fiber can be expected.

In the present invention, a conditioning composition means a composition used for a hair or fiber conditioning effect.

An alkyl ketene compound used in the present invention may be represented by Chemical Formula 1 below.

[Chemical Formula 1]

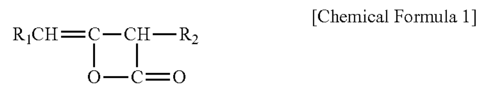

In Chemical Formula 1, $R_1$ and $R_2$ may each be independently a saturated or unsaturated alkyl having 1 to 40 carbon atoms or a saturated or unsaturated fatty acid having 1 to 40 carbon atoms.

In the present invention, "alkyl" refers to a straight-chain, branched-chain or cyclic hydrocarbon having a specified number of carbon atoms unless otherwise specified.

In the present invention, "fatty acid" refers to a carboxylic acid having a specified number of carbon atoms unless otherwise specified. In this case, the specified number of carbon atoms may have a straight-chain or branched-chain structure.

In one embodiment, $R_1$ and $R_2$ may each be independently a straight-chain or branched-chain saturated or unsaturated alkyl having 8 to 22 carbon atoms or a straight-chain or branched-chain saturated or unsaturated fatty acid having 8 to 22 carbon atoms. Preferably, it may be selected from the group consisting of a straight chain saturated or unsaturated alkyl having 16 to 18 carbon atoms and 18-methyleicosanoic acid (18-MEA), and most preferably 18-methyleicosanoic acid (18-MEA).

In addition to the alkyl group or fatty acid, $R_1$ and/or $R_2$ may include a nucleophilic group, such as an alcohol at the terminal of a 2-oxetanone dimer, and the alkyl group of the alcohol may include functional groups, such as esters and ethers. It may also include ethoxylated (eO/PO addition) or hydrogenated alcohols.

In one embodiment, the alkyl ketene compound may include one or more selected from the group consisting of, for example, alkyl ($R_1$, $R_2$; C12-16) ketenes, hydrogenated tallow fatty acid ($R_1$, $R_2$; C12-16) diketenes ($R_1$, $R_2$; fatty acids, tallow, hydrogenated, dimers, diketene derivatives), alkyl ($R_1$, $R_2$; C14-16) ketenes, alkyl ($R_1$, $R_2$; C16-18) ketenes, alkyl ($R_1$, $R_2$; C20-22) ketenes, alkyl ($R_1$, $R_2$; C14) ketenes, alkyl ($R_1$, $R_2$; C16) ketenes, alkyl ($R_1$, $R_2$; C18) ketenes, alkyl ($R_1$, $R_2$; C22) ketenes, alkyl ($R_1$; C14, $R_2$; C16) ketenes, alkyl ($R_1$; C16, $R_2$; C14) ketenes, alkyl ($R_1$; C16, $R_2$; C18) ketenes, alkyl ($R_1$; C18, $R_2$; C16) ketenes, alkyl ($R_1$, $R_2$; C18-MEA) ketenes, alkyl ($R_1$; C16, $R_2$; C18-MEA) ketenes, alkyl ($R_1$; C18, $R_2$; C18-MEA) ketenes, alkyl ($R_1$; C22, $R_2$; C18-MEA) ketenes, alkyl ($R_1$; C18-MEA, $R_2$; C16) ketenes, alkyl ($R_1$; C18-MEA, $R_2$; C18) ketenes and alkyl ($R_1$; C18-MEA, $R_2$; C22) ketenes, but is not limited thereto, and various types of alkyl ketene compounds can be used. In this case, for example, "C12" means a saturated or unsaturated alkyl having 12 carbon atoms, "C12-16" means a mixture of saturated or unsaturated alkyls having 12 to 16 carbon atoms, and "C18-MEA" means 18-methyleicosanoic acid (18-MEA). In addition, "alkyl ($R_1$; C18, $R_2$; C16) ketenes" means that in the compound of Chemical Formula 1, $R_1$ is a saturated or unsaturated alkyl having 18 carbon atoms and $R_2$ is a saturated or unsaturated alkyl having 16 carbon atoms, and "alkyl ($R_1$, $R_2$; C14) ketenes" means that in the compound of Chemical Formula 1, $R_1$ and $R_2$ are each a saturated or unsaturated alkyl having 14 carbon atoms.

In one embodiment, the content of the alkyl ketene compound is not particularly limited, and may be 0.0001 to 10 parts by weight, 0.01 to 7 parts by weight, or 0.1 to 5 parts by weight based on 100 parts by weight of the total composition. When the content is less than 0.0001 parts by weight, it is difficult to show a continuous conditioning effect, and when the content exceeds 10 parts by weight, there is a problem in that the unreacted compounds are lost.

The alkyl ketene compound can be applied to the hair or fiber to form a covalent bond with a protein residue in the hair or fiber. Through this, it is possible to maximize a conditioning effect of the hair or fiber.

In the present invention, an alkyl ketene compound represented by Chemical Formula 1 may be included in a hair or fiber treatment composition in the form of a previously dispersed, emulsified or encapsulated form.

When used in a dispersed and emulsified form, the composition may include a dispersing agent and an emulsifying agent, and conventionally used dispersing agents and emulsifying agents may be used as the dispersing agent and emulsifying agent. For example, anionic surfactants, such as sodium lauryl sulfate, fatty acid soaps, such as palmitic acid and stearic acid, nonionic surfactants, such as ethoxylated fatty alcohol, glyceryl ester, sorbitan esters of fatty acids, cationic surfactants, such as quaternary ammonium salts, and cationic polymers, such as cationic starch and cationic cellulose may be used. Specifically, one or more selected from the group consisting of glycerin fatty acid ester, polyoxyethylene fatty acid ester, polyoxyethylene sorbitan fatty acid ester, and polyoxyethylene alkylphenyl ether may be used as a nonionic surfactant (emulsifier), but are not limited thereto.

In addition, when used in an encapsulated form, the alkyl ketene compound may be diluted with a liquid hydrocarbon, ester oil, silicone oil, or the like, and encapsulated with gelatin, carrageenan, agar, silica, or the like. The encapsulation technology is not limited to the listed examples, and formulation technology commonly used in cosmetics may be applied.

The composition according to the present invention may further include one or more selected from the group consisting of a cationic surfactant and an anionic surfactant. A conditioning effect can be further improved by further including the above components.

The composition according to the present invention may further include, without limitation, those which can be commonly used in hair or fiber treatment compositions as a cationic surfactant, and for example, one or more selected from the group consisting of alkyltrimethylammonium salts, dialkyldimethyl ammonium salts, alkyldimethylbenzylammonium salts, esterquats, alkylpyridinium salts, alkyl imidazolinium salts, alkylamine salts and fatty acids, preferably dialkyldimethyl ammonium salts, alkyl imidazolinium salts, and esterquats, more preferably esterquats may be used.

In the present invention, by using an alkyl ketene compound and a cationic surfactant in combination, it is possible to help the alkyl ketene compound more easily act on a substrate due to the interaction between the alkyl ketene compound and a hydrophobic portion of a cationic surfactant. Through this, it is expected that more excellent effects can be exhibited than when each is prescribed and used alone, but the present invention is not limited to the above theory.

In addition, the composition according to the present invention may further include, without limitation, those which may be commonly used in hair or fiber treatment compositions as an anionic surfactant, and for example, one or more selected from the group consisting of soap, alkyl sulfates, alkylether sulfates, alkylbenzene sulfonates, alkane sulfonates, alpha olefin sulfonates, alpha sulfo fatty acid ester salts, alkyl sulfoacetates, alkyl sulfosuccinates, alkyl ether sulfosuccinates, alkyl phosphates, alkyl ether phosphates, alkyl ether carboxylates, acyl lactate, acyl taurate, acyl glutamate, acyl alaninate, acyl isethionate and acyl sarcosinate may be used. Preferably, soap, alkyl ether sulfates, and alkylbenzene sulfonates may be used, and more preferably, alkylbenzene sulfonates may be used.

In the present invention, by using an alkyl ketene compound and an anionic surfactant in combination, the anionic surfactant can help the alkyl ketene compound to more easily act on a substrate by removing lipids from the substrate. Through this, it is expected that more excellent effects can be exhibited than when each is prescribed and used alone, but the present invention is not limited to the above theory.

In one embodiment, the content of a cationic surfactant and/or an anionic surfactant is not particularly limited, and may be 0.01 to 50 parts by weight, 1 to 30 parts by weight, or 10 to 20 parts by weight based on 100 parts by weight of the total composition. A better conditioning effect can be provided within the content range.

A composition according to the present invention may further include water soluble cellulose derivatives, such as hydroxy ethyl-, hydroxy propyl-, and carboxy methyl cellulose and dispersion and emulsion stabilizers, such as starch, xanthan gum, polyvinyl alcohol, arylate polymers, and carboxy vinyl polymers.

The composition according to the present invention may further include a fragrance. The type of fragrance is not particularly limited as long as it can be used in a hair or fiber treatment composition, and a fragrance having a log P value of −1.0 to 4.5 may be used.

P is a fractionation coefficient and represents the solubility of the compound in two solvents. For example, P may be a ratio of compound solubility in octanol and compound solubility in water. When the compound is lipophilic, the P value can be very large, so it can be expressed as a log P value. Preferably, the log P value of the fragrance may be 0.5 to 4.5, 0.7 to 4.5, 1.0 to 4.4 or 2.0 to 4.4.

In one embodiment, the fragrance may include one or more compounds selected from the group consisting of, for example, (2-tert-butylcyclohexyl) acetate, (3-oxo-2-pentylcyclopentyl)acetic acid, (E)-4-decanal, 1-(1,2,3,4,5,6,7,8-octahydro-2,3,8,8-tetramethyl-2-naphthalenyl)ethanone, 1-(2,6,6-trimethyl-1-cyclohex-3-cenyl)-2-buten-one, 1-(2,6,6-trimethyl-2-cyclohexen-1-yl)penten-3-one, 1,2-dichloroethane, 1,3,3-trimethyl-2-oxabicyclo[2,2,2]octane, 1,4-dioxane, 1,6-hexanediol diglycidyl ether, 1,7,7-trimethylbicyclo[2.2.1]hept-2-yl acetate, 10-undecenal, 17a-hydroxyprogesterone, 1-bromoethane, 1-bromopentane, 1-butanol, 1-butene, 1-chlorohexane, 1-fluorooctane, 1-heptanol, 1-heptene, 1-hexanol, 1-hexene, 1-iodobutane, 1-methoxypropan-2-ol, 1-naphthol, 1-nonanol, 1-octanol, 1-octyne, 1-pentanol) (1.56), 1-pentene) (2.80), (1-propanol) (0.25), 2-(2-butoxyethoxy)ethanol (0.65), 2-(dimethylamino)-5,6-dimethylpyrimidin-4-ol (1.63), 2-(ethoxycarbonyl)benzoic acid (1.80), (2,2,2-trichloro-1-phenylethanol, 2,3-butanediol, 2,4,6-trichlorophenol, 2,4-dichlorophenol, 2,4-dichlorophenoxyacetic acid, 2,4-dihydroxy-3,6-dimethylbenzoic acid, 2,4-dimethylcyclohex-3-ene-1-carbaldehyde, 2,6-dimethyl-2-heptanol, 2-butanol, 2-butanone, 2-butoxyethanol, 2-butyne, 2-chlorophenol, 2-cresol, 2-decanone, 2-ethoxy ethanol, 2-ethyl-1-hexanol, 2-ethylhexene, 2-heptanone, 2-hexanol, 2-hexanone, 2-hexen-1-ol, 2-hydroxybenzoic acid, 2-iodobutane, 2-isopropoxyethanol, 2-isopropoxyphenol, 2-MeTHF, 2-methoxy-4-(2-propenyl)-phenol, 2-methoxy-4-propylphenol, 2-methoxy-4-vinylphenol, 2-methoxyethanol, 2-methoxyethyl acetate, 2-methyl-1-butanol, 2-methyl-1-propanal, 2-methyl-2-butanol, 2-methyl-2-pentanol, 2-methyl-2-propanol, 2-methylbutyl acetate, 2-methylbutyric acid, 2-methylpropane, 2-methylpropionic acid, 2-naphthol, 2-naphthylamine, 2-nitro-4-phenylenediamine, 2-nonanone, 2-octanone, 2-octyne, 2-pentanone, 2-phenoxyethanol, 2-phenyl-1-ethanol, 2-phenylphenol, 2-propanol, 2-undecanone, 3 (4)-(4-hydroxy-4-methylpentyl)-3-cyclohexene-1-carboxaldehyde, 3-(4-tert-butylphenyl)-2-methylpropanal (Lilial), 3,4-xylenol, 3,7-dimethyloct-6-en-1-ol, 3,7-dimethylocta-2,6-dienal, 3,7-dimethyloctan-3-ol, 3-cresol, 3-hexanol, 3-hexanone, 3-methyl-1-butanol, 3-methyl-3-pentanol, 3-methylbutyl acetate, 3-methylbutyric acid, 3-nitrophenol, 3-phenyl butanal, 3-phenyl-1-propanol, 4-(2,6,6-trimethyl-1-cyclohexene-1-yl)-3-butene-2-one, 4-(methylthio)-3,5-xylenol, 4-acetamidophenol, 4-amino-2-nitrophenol, 4-aminobenzoic acid, 4-aminophenol, 4-bromophenol, 4-chloro-3-xylenol, 4-chlorocresol, 4-chlorophenol, 4-cresol, 4-cyanophenol, 4-ethoxy-4-oxobut-2-enoic acid, 4-ethyl phenol, 4-heptyloxyphenol, 4-iodophenol, 4-methoxy acetophenone, 4-methoxybenzyl alcohol, 4-methylpentanoic acid, 4-nitroaniline, 4-nitrophenol, 4-pentyloxyphenol, 5-fluorouracil, 5-hexyloxolan-2-one, acetaldehyde, acetic acid, acetone, acetonitrile, acetophenone, acetyl cedrene, acetylcysteine, acetylsalicylic acid, allyl alcohol, allyl heptanoate, alpha terpineol, amobarbital, amyl alcohol, amyl salicylate, androstenedione, anethole USP, aniline, α-terpineol, atrazine, atropine, azodrin, barbital, benzaldehyde, benzene, benzocaine, benzoic acid, benzoic acid, 2-amino-, dihydrochloride, benzophenone, benzyl acetate, benzyl alcohol, benzyl benzoate, benzyl nicotinate, benzyl salicylate, beta terpineol, beta-estradiol, boric acid, butachlor, butobarbital, butyl 4-hydroxybenzoate, butyl acetate, butyl alcohol, butyl nicotinate, butyraldehyde, butyric acid, caffeine, carbamic acid, dimethyl-, carbamic acid, dimethyl, ethylester, carbaryl, carvone, catechol, chloramphenicol, chlorocresol, chloroform, chloroxylenol, chlorpheniramine, cinnamic acid, cinnamic aldehyde, cinnamic alcohol, cinnamyl alcohol, cinnamyl anthranilate, cis-1,3-dichloropropene, cis-3-Hexenyl acetate, cis-6-nonenal, cis-jasmone, codeine, cortexone, coumarin, cumene, cyclododecanone, cyclohexane, cyclohexanone, cyclopentanone, cycloundecanone, decanal, decanoic acid, deoxycorticosterone, diisopropyl fluorophosphate (dFP), dihydroepiandrosterone (DHEA), diazinon, dichloromethane, diclofenac, diethyl ether, diethyl maleate, diethyl malonate, diethyl phthalate, diethylene glycol monobutyl ether, diethylene glycol monobutyl ether acetate, diethylether, dihydro linalool, dihydromyrcenol, dihydro-α-terpineol, dimethoate, dimethyl benzyl carbinyl acetate, dimethyl carbonate, dimethylcyclohexanol, dimethylethylamine, dimethylformamide, dimethylnitrosamine, dinitrochlorobenzene, diphenyl ether, dipropylene glycol methyl ether, dl-Citronellol, d-limonene, dimethyl phthalate (dMP), E-2-butenal, E-2-hexenal, E-2-octene, ethylene glycol, ephedrine, estradiol, estragole, estriol, estrone, ethane, ethanol, ethyl acetate, ethyl benzene, ethyl ether, ethyl hydrogen malonate, ethyl nicotinate, ethyl vanillin, ethylbenzene, ethylene glycol methyl ether, ethynylbenzene, eucalyptol, eugenol, eugenyl methyl ether, flor acetate, flutamide, geraniol, geranyl nitrile, glycerol formal, hedione, heptanal, heptane, heptanoic acid, heptanol, hexanal, hexanoic acid, hexanol, hippuric acid, hydrochloric acid, hydroxycitronellal, ibuprofen, indole, iodomethane, isoeugenol, isobutyl isobutyrate, isobutyl salicylate, isoeugenol, isopentyl, isovalerate, isoquinoline, koavone, lactic acid, LIFFAROME, linalool, lindane, malathion, maleic acid, malonic acid, 4,4'-methylene bis(2-chloroaniline) (mbOCA), m-Cresol, MDA, meperidine, mesitylene, methanol, methiocarb, methyl 2-(3-oxo-2-pentylcyclopentyl)acetate, methyl 2-nonynoate, methyl acetate, methyl anthranilate, methyl atrarate, methyl benzoate, methyl beta naphthyl ketone, methyl dihydrojasmonate, methyl isobutyl ketone, methyl N-methylanthranilate, methyl nicotinate, methyl propionate, methyl salicylate, methyl tert-butyl ether, methyl-4-hydroxy benzoate, methyl-4-OH benzoate, methyl-parathion, methyl salicylate, morphine, musk ketone, m-xylene, N,N-diethyl-m-toluamide, Naproxen, n-butane, n-butanol, n-decanol, Nerol, n-heptane, n-heptanol, n-hexane, n-hexanol, N-hexyl nicotinate, nicotinamide, nicotine, nicotinic acid, nitrobenzene, nitroglycerine, N-methyl pyrrolidone, N-methylcarbamate, n-Nonanol, n-octanol, nonalactone, nonanoic acid, n-pentane, n-pentanol, N-phenyl-2-naphthylamine, n-propanol, n-propoxyethanol, o-chlorotoluene, o-cresol, o-cresyl glycidyl ether, octanal, octanoic acid, octanol, orange flower ether phenyl ethyl acetate, o-toluidine, o-xylene, paraoxon, parathion, p-cresol, pentanoic acid, pentanol, phenethyl alcohol, phenobarbital, phenol, phenoxanol, phenoxy ethyl isobutyrate, phenyl ethyl alcohol, phenyl propyl alcohol, phenylethyl alcohol, phosmet, phoxim, phthalic acid, pirimicarb, pregnenolone, progesterone, prop-2-enyl heptanoate, propane, propenal, propene, propionaldehyde, propionic acid, propoxur, propranolol, propyl acetate, propyl butyrate, propyl formate, propylene carbonate, propylene glycol, p-t-butyl-α-methylhydrocinnamic aldehyde, p-xylene, pyridine, resorcinol, safrole, salicylic acid, scopolamine, styrene, terpinen-4-ol, tert-butanol, testosterone, tetrahydrofuran, tetrahydrolinalool, theophylline, thymol, toluene, triacetin, trichloromethane, trichloromethyl phenyl carbinyl acetate, triclopyr, tricyclododecenyl acetate, triethanolamine, trifluoroacetic acid, trimethylamine, undecanoic acid, valeric acid, vanillin and α-methyl-1,3-benzodioxolE-5-propionaldehyde.

In one embodiment, the content of the fragrance is not particularly limited, and may be 0.0001 to 30 parts by weight based on 100 parts by weight of the total composition.

In addition, incidentally, the composition according to the present invention may further include, in order to increase stabilization and a conditioning effect incidentally, cationized polymers, such as fatty acids, fatty alcohols, cationized starch, cationized cellulose, cationized guar, cationized acrylate and acrylamide, polyvinylpyrrolidone, and the like, and silicone. In addition, components for formulation, such as solvents, surfactants, thickeners, stabilizers, preservatives, colorants, pH adjusters, metal ion sequestering agents, pearlescent agents, appearance improvers, pigments and powder particles may be further included for formulation.

When the composition according to the present invention is used as a hair treatment composition, that is, a hair conditioning cosmetic composition, the formulation is not particularly limited, and all formulations, such as shampoos, rinses, treatments, hair packs, hair essences, waxes, gels and sprays, can be included.

In addition, in the present invention, when the composition is used as a fiber treatment composition, it may generally include components that impart functions, such as cleaning, tidying, and pointing use for fiber care, and components that impart beneficial functions to fibers, such as dyeing, bleaching, softening, sterilizing UV protection, fragrance, and the like. A formulation of the fiber treatment composition is not particularly limited, and examples of application include products, such as detergents, softeners, fiber rinses, treatments, and partial treatment agents.

Each of the above-mentioned components included in the composition according to the present invention may preferably be included in the composition of the present invention within a range not exceeding the maximum amount specified in standards prescribed by each government. For example, in the case of providing a pharmaceutical composition, it may be included in the present invention within the scope of the preparation method, properties, usage amount, and the like specified in the pharmacopoeia or pharmaceutical code prescribed in Korea, the United States, Europe, Germany, Japan, China, and the like. In addition, in the case of providing a cosmetic composition, it is included in the cosmetic composition of the present invention within a range that does not exceed the maximum amount specified in the Cosmetics Safety Act prescribed by the government of each country or (Cosmetics Safety Technical Specifications) prescribed by the Chinese government.

In addition, the present invention relates to a conditioning method for treating hair or fibers with the aforementioned hair or fiber treatment composition.

In the present invention, the treatment may use application, spreading, or other methods similar thereto.

When hair or fiber are treated with the hair or fiber treatment composition according to the present invention, the alkyl ketene compound represented by Chemical Formula 1 forms a covalent bond with the protein residue of the hair or fiber. Through this, permanent hydrophobicity can be imparted to hair or fiber, and the conditioning effect can be sustained.

The active group (lactone ring) of the alkyl ketene compound may bind to hair or a fiber in a form of a fixed covalent bond by an esterification reaction with a hydroxyl group in hair or the fiber. Specifically, the alkyl ketene compound may form a covalent bond with a hydroxyl group to impart hydrophobicity to a surface, increase rigidity, and does not impair flexibility.

In the present invention, the treatment temperature, that is, a temperature when the hair or fiber treatment composition according to the present invention is treated, is not particularly limited, and may be 20 to 250° C., preferably 30 to 230° C., more preferably 80 to 120° C. In the above temperature range, it is possible to provide a continuous conditioning effect by increasing the permanent bonding efficiency between the compound and the hair or fiber.

For example, the composition of the present invention can prevent and/or improve hair or fiber damage caused by heat.

Also, as an example, the composition of the present invention can maintain a residual fragrance in hair or fibers, and also enhance flexibility, softness, hydrophobicity and/or an anti-shrinkage property of the hair or fiber.

MODES OF THE INVENTION

Hereinafter, the present invention will be described in detail by way of Examples. The following Examples merely illustrate the present invention, but the scope of the present invention is not limited by the following Examples. The examples are merely provided to complete the disclosure of the present invention and to fully convey the scope of the invention to those skilled in the art, and the invention is only defined by the scope of the claims.

Hereinafter, materials used in the Examples and Comparative Examples of the present invention were purchased and used from general raw material purchasing places.

EXAMPLES

Preparation Example 1. Preparation of Hair Treatment Composition (Examples 1 to 8 and Comparative Examples 1 to 6)

Hair treatment compositions (Examples 1 to 8 and Comparative Examples 1 to 6) including the components in Tables 1 and 2 below were prepared. In Table 2 below, an alkyl ketene compound is a compound having a structure of Chemical Formula 1, and $R_1$ and $R_2$ are described.

First, a fatty acid or an alkyl ketene compound, a nonionic emulsifier, and a thickener were added to purified water, heated to 70° C., sufficiently stirred, and then cooled to room temperature (25° C.) to prepare a composition.

TABLE 1

| | Component | Content (% by weight) |
|---|---|---|
| Nonionic emulsifier | Glycerin fatty acid ester | 0.25 |
| | Polyoxyethylene fatty acid ester | 0.25 |
| Thickener | Higher alcohol | 5.0 |
| Fatty acid or alkyl ketene compound | See Table 2 | Comparative Example: 3.0<br>Example: 1.5 |
| | Water | to 100 |

TABLE 2

| Classification | Fatty acid or alkyl ketene compound | |
|---|---|---|
| | $R_1$ and $R_2$ | Compound name |
| Comparative Example 1 | Fatty acid (C14) | Myristic acid |
| Comparative Example 2 | Fatty acid (C16) | Palmitic acid |

TABLE 2-continued

| Classification | Fatty acid or alkyl ketene compound | |
|---|---|---|
| | $R_1$ and $R_2$ | Compound name |
| Comparative Example 3 | Fatty acid (C18) | Stearic acid |
| Comparative Example 4 | Fatty acid (C16 50% + C18 50%) | — |
| Comparative Example 5 | Fatty acid (C18-MEA) | 18-methyleicosanoic acid |
| Comparative Example 6 | Fatty acid (C16 50% + C18-MEA 50%) | — |
| Example 1 | Alkyl ($R_1$, $R_1$; C12-16) ketene | C12-16 alkyl ketene dimer |
| Example 2 | Alkyl ($R_1$, $R_2$; C16-18) ketene | C16-18 alkyl ketene dimer |
| Example 3 | Alkyl ($R_1$, $R_2$; C16) ketene | C16 alkyl ketene dimer |
| Example 4 | Alkyl ($R_1$, $R_2$; C18) ketene | C18 alkyl ketene dimer |
| Example 5 | Alkyl ($R_1$; C16, $R_2$; C18) Ketene | C16 alkyl/C18 alkyl ketene dimer |
| Example 6 | Alkyl ($R_1$, $R_2$; C18-MEA) ketene | 18-methyleicosanoyl ketene dimer |
| Example 7 | Alkyl ($R_1$; C16, $R_2$; C18-MEA) ketene | C16 alkyl/18-methleicosanoyl ketene dimer |
| Example 8 | Alkyl ($R_1$; C18-MEA, $R_2$; C16) ketene | 18-methleicosanoyl/C16 alkyl ketene dimer |

Experimental Example 1. Comparison of Conditioning Effects of Hair Treatment Compositions (1) Method 1 g of each prepared hair treatment composition of Examples 1 to 8 and Comparative Examples 1 to 6 was evenly applied on about 4 g of a hair tress, left at room temperature for 30 minutes to induce a reaction, and an initial conditioning effect (hair smoothness satisfaction immediately after use_satisfaction 1) was compared by washing with running water and shampoo first.

Thereafter, shampooing was performed once a day, and after 10 days, a hair conditioning effect (satisfaction with hair smoothness after shampooing 10 times_satisfaction 2) was compared.

The conditioning effect was evaluated and compared by sensory evaluation on a 5-point scale (5 very good, 4 slightly good, 3 no difference, 2 ineffective, 1 very ineffective).

(2) Results

The satisfaction evaluation results are shown in Table 3 below.

As shown in Table 3, it can be confirmed that Examples 1 to 8 using an alkyl ketene compound exhibited better conditioning effects and sustained conditioning effects than Comparative Examples 1 to 6 not including the alkyl ketene compound.

Experimental Example 2. Comparison of Conditioning Effects of Hair Treatment Compositions According to Treatment Temperature (1) Method Using the compositions of Examples 1 to 8, 1 g of each composition was evenly applied on about 4 g of a hair tress, and dried with a hair dryer at a temperature of 80 to 100° C. for 5 minutes to apply heat.

After treatment, hair was first washed with running water and shampoo, and an initial conditioning effect (hair smoothness satisfaction immediately after use_satisfaction 1) was compared.

Thereafter, shampooing was performed once a day, and after 10 days, a hair conditioning effect (satisfaction with hair smoothness after shampooing 10 times_satisfaction 2) was compared.

The conditioning effect was evaluated and compared by sensory evaluation on a 5-point scale (5 very good, 4 slightly good, 3 no difference, 2 ineffective, 1 very ineffective).

(2) Results

The satisfaction evaluation results are shown in Table 4 below.

As shown in Table 4, it can be confirmed that a hair tress containing the alkyl ketene compounds of Examples and treated at 80 to 100° C. for 5 minutes using a hair dryer has relatively excellent conditioning effects and durability compared to the case of drying at room temperature using the same composition.

Accordingly, it can be confirmed that when heat treatment conditions are added, covalent bond formation efficiency between an alkyl ketene compound and hair is better, resulting in a better conditioning effect and a lasting effect. That is, when a composition according to the present invention is used, hair is not damaged by heat, but a surprising effect of further improving the conditioning effect is shown.

TABLE 3

| Satisfaction (n = 10) | Comp Ex. 1 | Comp. Ex. 2 | Comp. Ex. 3 | Comp. Ex. 4 | Comp. Ex. 5 | Comp. Ex. 6 | Ex. 1 | Ex. 2 | Ex. 3 | Ex. 4 | Ex. 5 | Ex. 6 | Ex. 7 | Ex. 8 |
|---|---|---|---|---|---|---|---|---|---|---|---|---|---|---|
| Satisfaction 1 | 3.0 | 3.0 | 3.5 | 3.5 | 3.5 | 3.5 | 4.0 | 4.0 | 4.0 | 4.5 | 4.0 | 5.0 | 4.5 | 4.5 |
| Satisfaction 2 | 2.5 | 2.5 | 2.5 | 2.5 | 2.8 | 2.8 | 3.0 | 3.0 | 3.0 | 3.3 | 3.0 | 3.5 | 3.3 | 3.3 |

Ex.: Example

Comp. Ex.: Comparative Example

TABLE 4

| Satisfaction (n = 10) | Example 1 | Example 2 | Example 3 | Example 4 | Example 5 | Example 6 | Example 7 | Example 8 |
|---|---|---|---|---|---|---|---|---|
| Satisfaction 1 | 4.0 | 4.0 | 4.0 | 4.5 | 4.0 | 5.0 | 4.5 | 4.5 |
| Satisfaction 2 | 3.5 | 3.5 | 3.5 | 4.0 | 3.5 | 4.0 | 4.0 | 4.0 |

Preparation Example 2. Preparation of Fiber Treatment Composition (Examples 9 to 16 and Comparative Examples 7 to 12)

Fiber treatment compositions (Examples 9 to 16 and Comparative Examples 7 to 12) including the components in Tables 5 and 6 below were prepared. In Table 6 below, an alkyl ketene compound is a compound having a structure of Chemical Formula 1, and $R_1$ and $R_2$ are described.

First, a fatty acid or an alkyl ketene compound, a nonionic emulsifier, and ethanol were added to purified water, heated to 70° C., sufficiently stirred, and then cooled to room temperature (25° C.) to prepare a composition.

TABLE 5

| | Component | Content (% by weight) |
|---|---|---|
| Nonionic emulsifier | Polyoxyethylene sorbitan fatty acid ester | 0.5 |
| | Polyoxyethylene alkylphenyl ether | 0.3 |
| Fatty acid or alkyl ketene compound | See Table 6 | Comparative Example: 2.0<br>Example: 1.0 |
| | Ethanol | 0.5 |
| | Water | to 100 |

TABLE 6

| Classification | Fatty acid or alkyl ketene compound | |
|---|---|---|
| | $R_1$ and $R_2$ | Compound |
| Comparative Example 7 | Fatty acid (C14) | Myristic acid |
| Comparative Example 8 | Fatty acid (C16) | Palmitic acid |
| Comparative Example 9 | Fatty acid (C18) | Stearic acid |
| Comparative Example 10 | Fatty acid (C16 50% + C18 50%) | — |
| Comparative Example 11 | Fatty acid (C18-MEA) | 18-methyleicosanoic acid |
| Comparative Example 12 | Fatty acid (C16 50% + C18-MEA 50%) | — |
| Example 9 | Alkyl ($R_1$, $R_1$; C12-16) ketene | C12-16 alkyl ketene dimer |
| Example 10 | Alkyl ($R_1$, $R_2$; C16-18) ketene | C16-18 alkyl ketene dimer |
| Example 11 | Alkyl ($R_1$, $R_2$; C16) ketene | C16 alkyl ketene dimer |
| Example 12 | Alkyl ($R_1$, $R_2$; C18) ketene | C18 alkyl ketene dimer |
| Example 13 | Alkyl ($R_1$; C16, $R_2$; C18) Ketene | C16 alkyl/C18 alkyl ketene dimer |
| Example 14 | Alkyl ($R_1$, $R_2$; C18-MEA) ketene | 18-methyleicosanoyl ketene dimer |
| Example 15 | Alkyl ($R_1$; C16, $R_2$; C18-MEA) ketene | C16 alkyl/18-methleicosanoyl ketene dimer |
| Example 16 | Alkyl ($R_1$; C18-MEA, $R_2$; C16) ketene | 18-methleicosanoyl/C16 alkyl ketene dimer |

Experimental Example 3. Comparison of Conditioning Effects of Fiber Treatment Compositions (1) Method 1 g of each prepared fiber treatment composition of Examples 8 to 16 and Comparative Examples 7 to 12 was evenly applied on standard wool fiber having a width×length of 20 cm×20 cm, left at room temperature for 30 minutes to induce a reaction, and an initial fiber softening effect (satisfaction of fiber softness immediately after use_satisfaction 1) was compared after washing with flowing water and detergent and drying.

Then, after washing with laundry detergent three times and drying, a fiber softening effect (fiber softness satisfaction after washing three times_satisfaction 2) was compared.

The fiber softening effect was evaluated and compared by sensory evaluation on a 5-point scale (5 very good, 4 slightly good, 3 no difference, 2 ineffective, 1 very ineffective).

(2) Results

The satisfaction evaluation results are shown in Table 7 below.

As shown in Table 7, it can be confirmed that Examples 1 to 8 using an alkyl ketene compound exhibited better fiber softening effects and sustained fiber softening effects than Comparative Examples 7 to 12 not including the alkyl ketene compound.

TABLE 7

| Satisfaction (n = 10) | Comp. Ex. 7 | Comp. Ex. 8 | Comp. Ex. 9 | Comp. Ex. 10 | Comp. Ex. 11 | Comp. Ex. 12 | Ex. 9 | Ex. 10 | Ex. 11 | Ex. 12 | Ex. 13 | Ex. 14 | Ex. 15 | Ex. 16 |
|---|---|---|---|---|---|---|---|---|---|---|---|---|---|---|
| Satisfaction 1 | 3.0 | 3.3 | 3.5 | 3.5 | 3.5 | 3.5 | 3.8 | 4.0 | 3.8 | 4.0 | 4.5 | 5.0 | 4.8 | 4.8 |
| Satisfaction 2 | 2.5 | 2.5 | 2.5 | 2.5 | 3.0 | 3.0 | 3.3 | 3.3 | 3.3 | 3.5 | 3.5 | 3.8 | 3.5 | 3.5 |

Comp. Ex.: Comparative Example
Ex.: Example

Experimental Example 4. Comparison of Conditioning Effects of Fiber Treatment Compositions According to Treatment Temperature (1) Method 1 g of each composition of Examples 9 to 16 was evenly applied on 1 g of standard wool fiber having a width×length of 20 cm×20 cm and the resultant was ironed for 1 minute with an iron at a temperature of about 150 to 170° C. to induce a reaction by heat.

After that, an initial fiber softening effect (fiber softness satisfaction immediately after use_satisfaction 1) was compared by washing with running water and detergent first.

Then, after washing with laundry detergent three times and drying, a fiber softening effect (fiber softness satisfaction after washing three times_satisfaction 2) was compared.

The fiber softening effect was evaluated and compared by sensory evaluation on a 5-point scale (5 very good, 4 slightly good, 3 no difference, 2 ineffective, 1 very ineffective).

(2) Results

The satisfaction evaluation results are shown in Table 8 below.

As shown in Table 8, wool fiber including an alkyl ketene compound and treated with an iron at 150 to 170° C. for 1 minute was evaluated as having better fiber softening effects and durability than when dried at room temperature using the same composition.

Accordingly, it can be confirmed that when heat treatment conditions are added, covalent bond formation efficiency between an alkyl ketene compound and wool fiber is better, resulting in a better fiber softening effect and a lasting effect. That is, when a composition according to the present invention is used, the fiber is not damaged by heat, but a surprising effect of further improving the conditioning effect is shown.

TABLE 8

| Satisfaction (n = 10) | Example 9 | Example 10 | Example 11 | Example 12 | Example 13 | Example 14 | Example 15 | Example 16 |
|---|---|---|---|---|---|---|---|---|
| Satisfaction 1 | 3.8 | 4.0 | 3.8 | 4.0 | 4.5 | 5.0 | 4.8 | 4.8 |
| Satisfaction 2 | 3.5 | 3.5 | 3.5 | 3.8 | 4.0 | 4.3 | 4.0 | 4.0 |

Additionally, compositions according to the Examples showed similar effects even when heat treatment was applied using a clothes dryer (LG Electronics-RH16VS).

Preparation Example 3. Preparation of Fiber Treatment Composition (Examples 17 to 23 and Comparative Examples 13 to 18)

Fiber treatment compositions (Examples 17 to 23 and Comparative Examples 13 to 18) including the components in Tables 9 and 10 below were prepared.

Alkylether sulfates, alkylbenzene sulfonates and soap are anionic surfactants, Dialkyldimethyl ammonium salts, alkyl imidazolinium salts and esterquats are cationic surfactants, and polyoxyethylene sorbitan fatty acid ester is a nonionic surfactant.

In addition, a C12-16 alkyl ketene dimer was used as an alkyl ketene compound.

First, an anionic surfactant or a cationic surfactant, a nonionic surfactant, and an alkyl ketene compound were added to purified water, heated to 70° C., and sufficiently stirred. Thereafter, the temperature was lowered to 40° C., and the mixture was sufficiently stirred by adding a fragrance, and then cooled to room temperature (25° C.) to prepare a composition.

TABLE 9

| Component | Example 17 | Example 18 | Example 19 | Example 20 | Example 21 | Example 22 | Example 23 |
|---|---|---|---|---|---|---|---|
| Alkyl ketene compound | 2.5 | 2.5 | 2.5 | 2.5 | 2.5 | 2.5 | 5.0 |
| Alkylether sulfate | 2.5 | — | — | — | — | — | — |
| Alkylbenzene sulfonate | — | 2.5 | — | — | — | — | — |
| soap | — | — | 2.5 | — | — | — | — |
| Dialkyl dimethyl ammonium salt | — | — | — | 2.5 | — | — | — |
| Alkyl imidazolinium salt | — | — | — | — | 2.5 | — | — |
| Esterquat | — | — | — | — | — | 2.5 | — |
| Polyoxyethylene sorbitan fatty acid ester | 0.5 | 0.5 | 0.5 | 0.5 | 0.5 | 0.5 | 0.5 |
| Fragrance | 0.5 | 0.5 | 0.5 | 0.5 | 0.5 | 0.5 | 0.5 |
| Purified water | Balance | Balance | Balance | Balance | Balance | Balance | Balance |

TABLE 10

| Component | Comparative Example 13 | Comparative Example 14 | Comparative Example 15 | Comparative Example 16 | Comparative Example 17 | Comparative Example 18 |
|---|---|---|---|---|---|---|
| Alkylether sulfate | 5.0 | — | — | — | — | — |
| Alkylbenzene sulfonate | — | 5.0 | — | — | — | — |
| soap | — | — | 5.0 | — | — | — |
| Dialkyldimethyl ammonium salt | — | — | — | 5.0 | — | — |
| Alkyl imidazolinium salt | — | — | — | — | 5.0 | — |
| Esterquat | — | — | — | — | — | 5.0 |
| Polyoxyethylene sorbitan fatty acid ester | 0.5 | 0.5 | 0.5 | 0.5 | 0.5 | 0.5 |
| Fragrance | 0.5 | 0.5 | 0.5 | 0.5 | 0.5 | 0.5 |
| Purified water | Balance | Balance | Balance | Balance | Balance | Balance |

Experimental Example 5. Evaluation of Fiber Property Improvement Effect According to Combination of Alkyl Ketene Compound and Surfactant For compositions of Examples 17 to 23, sensory evaluation (Residual fragrance strength, flexibility), stiffness, coefficient of friction, contact angle, and shrinkage were evaluated.

Sample treatment proceeded as follows.

First, a fiber treatment composition was diluted 10 times.

A standard cotton cloth (E-211, Center For Testmaterials BV, Netherlands) having a width×length of 8 cm×8 cm was immersed in the diluted fiber treatment composition, and stirred with a magnetic bar at a speed of 400 rpm and 35° C. for 1 hour. After that, the cotton cloth was taken out, rinsed with running tap water for 3 minutes, wiped dry with a kitchen towel, and put into a drying oven at 60° C. to dry for 2 hours. After storage for 24 hours under conditions of 25° C. and 50% RH, a test for each evaluation item was conducted.

(1) Sensory Evaluation

① Method (a) Sensory evaluation was performed on intensity and softness of the fragrance remaining on the cotton cloth after sample treatment, and a score from 1 to 5 was given. The evaluation was performed by experienced panelists, and an average value of 10 repetitions was obtained.

(b) In addition, the cotton cloth was treated with a 15% SLES solution three times in the same manner as the sample treatment method, washed and dried three times, and sensory evaluation was performed in the same manner as in (a).

Residual fragrance strength 1 almost no scent, 2 weak scent, 3 moderate scent, 4 strong scent, 5 very strong scent Flexibility: 1 very stiff, 2 moderately stiff, 3 normal, 4 moderately flexible, 5 very flexible ② Result The sensory evaluation results are shown in Tables 11 and 12 below.

As shown in the tables, it can be confirmed that Example 23 using an alkyl ketene compound alone and Examples 17 to 22 using an alkyl ketene compound and a surfactant together have higher residual fragrance strength and flexibility scores compared to Comparative Example. In particular, it can be confirmed that when the alkyl ketene compound and the surfactant are used together, it has better residual fragrance strength and flexibility.

These results maintained the above trend even after washing.

TABLE 11

| Classification | | Example 17 | Example 18 | Example 19 | Example 20 | Example 21 | Example 22 | Example 23 |
|---|---|---|---|---|---|---|---|---|
| Residual fragrance strength (points) | after treatment | 4.3 | 4.3 | 4.5 | 4.5 | 4.5 | 4.5 | 4.0 |
| | After 3 washes | 2.5 | 2.5 | 2.5 | 2.5 | 2.5 | 2.5 | 2.0 |
| Flexibility (points) | after treatment | 4.0 | 4.0 | 4.3 | 4.5 | 4.3 | 4.5 | 4.0 |
| | After 3 washes | 3.3 | 3.3 | 3.3 | 3.5 | 3.3 | 3.3 | 3.0 |

TABLE 12

| Classification | | Comparative Example 13 | Comparative Example 14 | Comparative Example 15 | Comparative Example 16 | Comparative Example 17 | Comparative Example 18 |
|---|---|---|---|---|---|---|---|
| Residual fragrance strength (points) | after treatment | 3.0 | 3.0 | 3.3 | 3.3 | 3.3 | 3.3 |
| | After 3 washes | 1.0 | 1.0 | 1.0 | 1.0 | 1.0 | 1.0 |
| Flexibility (points) | after treatment | 3.0 | 3.0 | 2.8 | 3.5 | 3.3 | 3.5 |
| | After 3 washes | 2.0 | 2.0 | 2.0 | 2.3 | 2.3 | 2.3 |

(2) Stiffness Evaluation

① Method (a) After sample treatment, the two facing sides of the cotton cloth are spread and fixed evenly on the two axes of a device (KES-FB2-S Pure Bending Tester, Kato Tech, Japan), and one axis is in a fixed state while the other axis rotates, and the moment M (gf cm/cm) applied when the cotton cloth is bent was recorded according to the curvature K ($cm^{-1}$) of the cotton cloth (Rotation range: K=±2.5 $cm^{-1}$, rotation speed: 0.5 $cm^{-1}$/sec).

(b) A slope value_1 was obtained through linear fitting for a section where the moment change amount was constant within the range of curvature K=0 to 2.5 $cm^{-1}$.

(c) The cotton cloth was rotated 90 degrees and processes (a) and (b) were repeated to obtain a slope value_2.

(d) Slope values_1 and 2 were geometrically averaged and expressed as stiffness (gf $cm^2$/cm) (average of 10 repetitions).

(e) In addition, the cotton cloth was treated with a 15% SLES solution three times in the same manner as the sample treatment method, washed and dried three times, and then stiffness was evaluated in the same manner as in (a) to (d) (average of 10 repetitions).

This experiment was performed at 25° C. and 50% RH.

② Result

Stiffness evaluation results are shown in Tables 13 and 14 below.

As shown in the tables, it can be confirmed that Example 23 using an alkyl ketene compound alone and Examples 17 to 22 using an alkyl ketene compound and a surfactant together have lower stiffness and are more flexible compared to Comparative Examples, and in particular, an effect is more excellent when an alkyl ketene compound and a surfactant are used together.

These results maintained the above trend even after washing. The results are similar to the above-mentioned flexibility sensory evaluation results.

TABLE 13

| Classification | | Example 17 | Example 18 | Example 19 | Example 20 | Example 21 | Example 22 | Example 23 |
|---|---|---|---|---|---|---|---|---|
| Stiffness (gf $cm^2$/cm) | After treatment | 0.757 | 0.726 | 0.735 | 0.642 | 0.654 | 0.667 | 0.801 |
| | After 3 washes | 0.697 | 0.686 | 0.704 | 0.608 | 0.606 | 0.622 | 0.772 |

TABLE 14

| Classification | | Comparative example 13 | Comparative example 14 | Comparative example 15 | Comparative example 16 | Comparative example 17 | Comparative example 18 |
|---|---|---|---|---|---|---|---|
| Stiffness (gf $cm^2$/cm) | After treatment | 1.104 | 1.080 | 1.048 | 0.956 | 0.938 | 0.923 |
| | After 3 washes | 0.974 | 0.959 | 0.944 | 0.845 | 0.869 | 0.850 |

(3) Coefficient of Friction Evaluation

① Method (a) A dedicated rubber probe, and a weight applying 200 g of normal force were installed on a friction tester (mTT175, Dia-Stron, UK), and a cotton cloth treated with a sample was spread flat and fixed to a moving plate of a device. The rubber probe was brought into contact with one end of the cotton cloth, and the frictional force generated between the rubber probe and the cotton cloth was recorded according to the position of the cotton cloth while moving the moving plate at a speed of 200 mm/min. The coefficient of friction was obtained from the average value of the frictional force and normal force in a specific range of the cotton cloth (average of 10 repetitions).

(b) In addition, the cotton cloth was treated with a 15% SLES solution three times in the same manner as the sample treatment method, washed and dried three times, and then a coefficient of friction was evaluated in the same manner as in (a) (average of 10 repetitions).

This experiment was performed at 25° C. and 50% RH.

② Result

Coefficient of friction evaluation results are shown in Tables 15 and 16 below.

As shown in the tables, it can be confirmed that Example 23 using an alkyl ketene compound alone and Examples 17 to 22 using an alkyl ketene compound and a surfactant together has a low coefficient of friction, and the fiber surface is less damaged and softer compared to Comparative Examples, and in particular, an effect is more excellent when an alkyl ketene compound and a surfactant are used together.

These results maintained the above trend even after washing.

TABLE 15

| Classification | | Example 17 | Example 18 | Example 19 | Example 20 | Example 21 | Example 22 | Example 23 |
|---|---|---|---|---|---|---|---|---|
| Coefficient of friction | After treatment | 0.7818 | 0.7735 | 0.7680 | 0.6128 | 0.6160 | 0.6271 | 0.8306 |
| | After 3 washes | 0.9067 | 0.9004 | 0.8911 | 0.7972 | 0.8113 | 0.8043 | 0.9372 |

TABLE 16

| Classification | | Comparative example 13 | Comparative example 14 | Comparative example 15 | Comparative example 16 | Comparative example 17 | Comparative example 18 |
|---|---|---|---|---|---|---|---|
| Coefficient of friction | After treatment | 1.0703 | 1.0445 | 1.0230 | 0.9195 | 0.9122 | 0.9039 |
| | After 3 washes | 1.0898 | 1.0812 | 1.0771 | 1.0669 | 1.0780 | 1.0804 |

(4) Contact Angle

① Method (a) After sample treatment, a cotton cloth was spread flat and placed on a parallel plate, then 10 μL of distilled water was dropped on each of 5 random locations, and images of the resulting droplets were taken using a Drop Shape Analyzer (DSA100, Kruss, Germany) and the contact angle was measured (average of 10 repetitions).

(b) In addition, the cotton cloth was treated with a 15% SLES solution three times in the same manner as the sample treatment method, washed and dried three times, and then a contact angle was evaluated in the same manner as in (a) (average of 10 repetitions).

This experiment was performed at 25° C. and 50% RH.

② Result

The contact angle evaluation results are shown in Table 17 below.

In Comparative Examples 13 to 18, in which only a surfactant was treated, the droplet was completely absorbed into the cotton cloth, so that contact angle measurement was not possible.

However, Example 23 using the alkyl ketene compound alone and Examples 17 to 22 using an alkyl ketene compound and a surfactant together showed a contact angle of 30° or more, through which it could be confirmed that a fiber surface was hydrophobic. In addition, it can be confirmed that surface hydrophobicity is maintained to some extent even after washing.

In particular, Examples 17 to 22 using an alkyl ketene compound and a surfactant show a contact angle close to 90° and a high contact angle even after washing, so that a long-lasting conditioning effect can be imparted through imparting hydrophobicity, which is the purpose of the present invention.

TABLE 17

| Classification | | Example 17 | Example 18 | Example 19 | Example 20 | Example 21 | Example 22 | Example 23 |
|---|---|---|---|---|---|---|---|---|
| Contact angle | After treatment | 87.04 | 87.75 | 89.71 | 89.96 | 89.03 | 90.26 | 67.92 |
| | After 3 washes | 80.57 | 81.21 | 79.95 | 82.10 | 80.63 | 81.25 | 44.84 |

(5) Shrinkage Evaluation

① Method (a) A fiber treatment composition prepared in Examples 17 to 23 and Comparative Examples 13 to 18 was used to treat standard wool fiber (537, Testfibers, Inc., USA).

A treatment method is the same as a treatment method described above in Experimental Example 5.

(b) After unfolding the wool fiber and holding one end of the wool fiber with tongs inside a device (Volume tester (Bolero Lite, BOSSA NOVA VISION, USA)) and suspending it, a picture was taken with a camera and an area of the wool fiber was measured, and the degree of shrinkage compared to an original area (8 cm×8 cm) was expressed as shrinkage (%) (average of 10 repetitions).

(c) In addition, the wool fiber was treated with a 15% SLES solution three times in the same manner as the sample treatment method, washed and dried three times, and then shrinkage was evaluated in the same manner as in (b) (average of 10 repetitions).

② Result

The shrinkage evaluation results are shown in Tables 18 and 19 below.

As shown in the tables, it can be seen that Example 23 using the alkyl ketene compound alone and Examples 17 to 22 using the alkyl ketene compound and a surfactant together had a low shrinkage rate and high fiber shrinkage prevention ability compared to the Comparative Example. In particular, it can be confirmed that the effect is more excellent when the alkyl ketene compound and the surfactant are used together.

These results maintained the above trend even after washing.

TABLE 18

| Classification | | Example 17 | Example 18 | Example 19 | Example 20 | Example 21 | Example 22 | Example 23 |
|---|---|---|---|---|---|---|---|---|
| Shrinkage (%) | After treatment | 4.41 | 3.88 | 3.50 | 3.04 | 3.95 | 3.48 | 5.57 |
| | After 3 washes | 11.91 | 12.41 | 11.30 | 10.39 | 10.71 | 9.88 | 14.16 |

TABLE 19

| Classification | | Comparative Example 13 | Comparative Example 14 | Comparative Example 15 | Comparative Example 16 | Comparative Example 17 | Comparative Example 18 |
|---|---|---|---|---|---|---|---|
| Shrinkage (%) | After treatment | 23.71 | 24.14 | 21.77 | 7.57 | 7.73 | 7.34 |
| | After 3 washes | 28.82 | 28.96 | 27.59 | 27.29 | 28.36 | 26.70 |

INDUSTRIAL APPLICABILITY

Since the hair or fiber treatment composition according to the present invention contains an alkyl ketene compound capable of covalently bonding with protein residues of hair or fibers, the alkyl ketene compound forms a covalent bond with the protein residues without damaging hair or fibers, and beneficial effects, such as long-lasting conditioning can be provided by imparting permanent hydrophobicity.

In addition, the hair or fiber treatment composition according to the present invention can prevent and/or improve damage to hair or fibers caused by heat.

In addition, the hair or fiber treatment composition according to the present invention can maintain a residual fragrance in hair or fibers, and can enhance flexibility, softness, hydrophobicity or an anti-shrinkage property.

The invention claimed is:

1. A hair treatment composition comprising an alkyl ketene compound represented by Chemical Formula 1:

[Chemical Formula 1]

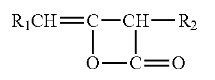

in Chemical Formula 1, $R_1$ and $R_2$ are each independently 18-methyleicosanoic acid (18-MEA), and further comprising one or more surfactants selected from the group consisting of a cationic surfactant and an anionic surfactant, for improving a conditioning effect.

2. The composition of claim 1, wherein the alkyl ketene compound is included in an amount of 0.0001 to 10 parts by weight based on a total weight of the hair treatment composition.

3. A method of conditioning hair, comprising applying to the hair the hair treatment composition of claim 1.

4. The method of claim 3, wherein the alkyl ketene compound in the hair treatment composition forms a covalent bond with the hair.

5. The method of claim 3, wherein the hair treatment composition is applied on the hair at a temperature of 20 to 250° C.

6. A method for preventing or improving thermal damage, comprising applying the hair treatment composition of claim 1 to hair.

7. A method for manufacture of a hair treatment composition, which comprises:

mixing an alkyl ketene compound represented by Chemical Formula 1:

[Chemical Formula 1]

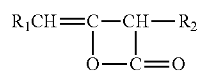

wherein in Chemical Formula 1, $R_1$ and $R_2$ are each independently 18-methyleicosanoic acid (18-MEA), and one or more surfactants selected from the group consisting of a cationic surfactant and an anionic surfactant, for improving a conditioning effect.

8. The method according to claim 7, wherein the alkyl ketene compound is included in an amount of 0.0001 to 10 parts by weight based on a total weight of the hair treatment composition.

9. A method for improving hair, comprising:

applying an effective amount of a hair treatment composition to hair, and applying a heat treatment, wherein the hair treatment composition comprises an alkyl ketene compound represented by Chemical Formula 1:

[Chemical Formula 1]

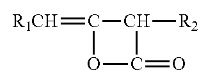

in Chemical Formula 1, $R_1$ and $R_2$ are each independently 18-methyleicosanoic acid (18-MEA), and one or more surfactants selected from the group consisting of a cationic surfactant and an anionic surfactant, for improving a conditioning effect.

* * * * *